US008541216B2

(12) United States Patent
Zhu et al.

(10) Patent No.: US 8,541,216 B2
(45) Date of Patent: Sep. 24, 2013

(54) INSECTICIDAL FERMENTATION BROTH FROM ACTINOMYCETES CONTAINING ENHANCED RATIO OF ACTIVE TO INACTIVE DUNAIMYCINS

(75) Inventors: Hong Zhu, West Sacramento, CA (US); Jorge Jimenez, Sacramento, CA (US); Colleen Taylor, Folsom, CA (US); Magalie Guilhabert-Goya, Davis, CA (US); Jonathan Margolis, Davis, CA (US)

(73) Assignee: Bayer CropScience LP, Davis, CA (US)

( * ) Notice: Subject to any disclaimer, the term of this patent is extended or adjusted under 35 U.S.C. 154(b) by 273 days.

(21) Appl. No.: 12/939,991

(22) Filed: Nov. 4, 2010

(65) Prior Publication Data

US 2011/0112185 A1 May 12, 2011

Related U.S. Application Data

(60) Provisional application No. 61/259,549, filed on Nov. 9, 2009, provisional application No. 61/258,716, filed on Nov. 6, 2009.

(51) Int. Cl.
*C12P 1/06* (2006.01)
(52) U.S. Cl.
USPC .................. 435/169; 435/142; 435/252.1
(58) Field of Classification Search
USPC ................. 435/169, 142, 252.1, 822
See application file for complete search history.

(56) References Cited

U.S. PATENT DOCUMENTS 5,362,634 A 11/1994 Boeck et al.
6,682,925 B1 * 1/2004 Lehman et al. ............ 435/253.5

FOREIGN PATENT DOCUMENTS

EP 1272611 B1 5/2006
JP 01-199988 A 8/1989

OTHER PUBLICATIONS

International Search Report and Written Opinion of the International Searching Authority, International Patent Application No. PCT/US2010/055499, Jul. 27, 2011, 9 pages.

International Preliminary Report on Patentability, International Patent Application No. PCT/US2010/055499, May 18, 2012, 5 pages.
Bueno, G., et al., "AQ6047: A Unique and Improved Strain of *Streptomyces galbus* with Insecticidal Activity", Poster Presentation at Entomological Society of America Meeting, Mar. 30, 2009, San Diego, California.
Burres, Neal S., et al., "Dunaimycins, A New Complex of Spiroketal 24-Membered Macrolides with Immunosuppressive Activity; III. Immunosuppressive Activities of Dunaimycins", The Journal of Antibiotics, Dec. 1991, pp. 1331-1341, vol. 44, No. 12, Tokyo, Japan.
Hochlowski, Jill E., et al., "Dunaimycins, A New Complex of Spiroketal 24-Membered Macrolides with Immunosuppressive Activity; II. Isolation and Elucidation of Structures", The Journal of Antibiotics, Dec. 1991, pp. 1318-1330, vol. 44, No. 12, Tokyo, Japan.
Karwowski, James P., et al., "Dunaimycins, A New Complex of Spiroketal 24-Membered Macrolides with Immunosuppressive Activity; I. Taxonomy of the Producing Organisms, Fermentation and Antimicrobial Activity", The Journal of Antibiotics, Dec. 1991, pp. 1312-1317, vol. 44, No. 12, Tokyo, Japan.
Le-Van, N., et al., "Streptosonin, A Novel Insecticidal Spiroketal Macrolide Isolated from *Streptomyces* Sp. S87-18203", Poster Presentation at the 10th IUPAC International Congress on the Chemistry of Crop Protection, Aug. 2002, Basel, Switzerland.
Lu, Tara, et al., "Formulation Development of a Microbial Based Bioinsecticide *Streptomyces galbus* AQ6047", AgraQuest, Inc. PowerPoint Presentation at ASTM, Oct. 13, 2010, San Antonio, Texas.
Marrone, P.G., and Jimenez, P.G., "Development of a Novel Microbial Biopesticide for the Control of Insect Pests", Commercialization Assessment Report to the USDA as a part of the SBIR phase II grant, prepared by Foresight Science and Technology, work performed between Sep. 2002 to Aug. 2004, <<http://www.reeis.usda.gov/web/crisprojectpages/193224.html>>.
Reddy, L., et al., "New Insecticidal Metabolites from Soil Isolate W719", The Journal of Antibiotics, Sep. 1991, pp. 962-968, vol. 44, No. 9, Tokyo, Japan.
Taylor, Colleen S., et al., "Use of Antibiotic Resistant Mutagenesis and Fed-Batch Fermentation to Enhance the Production of Insecticide Macrolides and Bioactivity by *Streptomyces galbus* AG6047", Poster Presentation at RAFT VIII (Recent Advances in Fermentation Technology)—Society of Industrial Microbiologists, Nov. 9, 2009, San Diego, California.
Mishra, S.K., et al, "Insecticidal and Nematicidal Properties of Microbial Metabolites," Journal of Industrial Microbiology, 1987, vol. 2, pp. 267-276.

* cited by examiner

*Primary Examiner* — Ralph Gitomer
(74) *Attorney, Agent, or Firm* — Michelle L. Samonek

(57) ABSTRACT

The present invention provides an insecticidal fermentation broth of an actinomycete, where the fermentation broth contains an optimized ratio of active dunaimycins to inactive dunaimycins.

11 Claims, 12 Drawing Sheets

Dunaimycin General Structure

| Compound | $R_1$ | $R_2$ | $R_3$ | $R_4$ | Insert |
|---|---|---|---|---|---|
| A1 | H | H | H | $CH_3$ | As shown |
| C1 | OH | H | H | $CH_3$ | As in A1 |
| C2 | OH | H | H | $CH_3$ | |
| C2S | OH | | H | $CH_3$ | As in C2 |
| D2 | OH | H | OH | $CH_3$ | As in C2 |
| D2S (Ossamycin) | OH | As in C2S | OH | $CH_3$ | As in C2 |
| D3 | OH | H | OH | $CH_3$ | |
| D3S | OH | As in C2S | OH | $CH_3$ | As in D3 |
| D4S | OH | As in C2S | OH | $CH_3$ | |

Figure 4

Bioactivity of Rifampicin Resistant Mutant vs Wild Type
Stage 3 Screening: Bioreactor Cultures

INSECTICIDAL FERMENTATION BROTH FROM ACTINOMYCETES CONTAINING ENHANCED RATIO OF ACTIVE TO INACTIVE DUNAIMYCINS

CROSS-REFERENCES TO RELATED APPLICATIONS

This application claims the benefit of U.S. Ser. No. 61/258,716, filed Nov. 6, 2009; and U.S. Ser. No. 61/259,549, filed Nov. 9, 2009, the contents of each are incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Insects cause over 22 billion dollars of crop damage in the United States alone. Many of the widely used insecticides are older neurotoxic compounds, and there is a substantial need for new, safer chemistries. Strain NRRL No. 30232 is a proprietary strain of *Streptomyces galbus* described in U.S. Pat. No. 6,682,925 that produces a group of closely related macrolides, called dunaimycins, exhibiting insecticidal activity, especially against Lepidoptera (caterpillars). Dunaimycins are 24-membered macrolides produced by actinomycetes that were first reported in the early 1990s by research groups at Abbott Laboratories. The Abbott researchers elucidated the structures of various dunaimycin species, A1, C1, C2, D2, D2S, D3 and D4S; studied their antimicrobial and immunosuppressive activities; and described the taxonomy of the producing organisms, two strains of *Streptomyces diastatochromogenes*. Karwowski, J. P., et al. *Journal of Antibiotics* December 1991, p. 1312-1317; Hochlowski, J. E., *Journal of Antibiotics*, December 1991, pp. 1318-1330; and Burres, N. S., et al., *Journal of Antibiotics*, December 1991, pp. 1331-1341. A few later publications described insecticidal or acaricidal activity of specific dunaimycins.

While the literature describes purification of specific dunaimycins and elucidation of their structure and activity, it lacks disclosures regarding interactions between the various species of dunaimycins and comparisons of insecticidal activity of the various dunaimycins. In addition, although production of fermentation broth containing dunaimycins in the gram per liter range is necessary to create a commercially viable insecticidal product, dunaimycin-related publications describe production of dunaimycins at milligram per liter levels. The background literature does not disclose methods for increasing dunaimycin production nor does it appreciate the corresponding challenges of scale-up.

In conducting experiments to increase dunaimycin production of *Streptomyces galbus* NRRL No. 30232 through screening of libraries of antibiotic-resistant mutants and optimizing fermentation conditions, Applicants increased dunaimycin production to previously unreported levels of at least 2.5 gram dunaimycin per liter fermentation broth (prior to concentration). Surprisingly, however, Applicants found that an increase in dunaimycin production was not necessarily proportional to an increase in insecticidal activity. Applicants analyzed in greater detail the interactions between the various species of dunaimycins and determined that particular dunaimycin species are insecticidally active, while others are either inactive or antagonistic to insecticidal activity.

BRIEF SUMMARY OF THE INVENTION

Therefore, the present invention relates to compositions comprising cultures of actinomycetes having an optimized ratio of insecticidally active to inactive dunaimycins. In one embodiment, such cultures contain gram per liter levels of dunaimycins.

This invention also relates to processes for producing fermentation broth enriched in insecticidally active dunaimycins by cultivating actinomycetes capable of producing both active and inactive dunaimycins in optimized culture media until at least about one gram total dunaimycins per one liter fermentation broth is produced. In one embodiment the optimized culture media contains carbon and nitrogen sources in a C:N ratio of at least 10:1, by weight. The weight ratios of C:N can be calculated by known methods based on the masses of C and N in the overall mix of the fermentation medium. Accordingly, multiple components can add different amounts to each of the C and N portions, but the overall ratio in the mixture will have the indicated ratio.

This invention also encompasses methods for producing dunaimycin-containing fermentation products using the above process and standard purification techniques to obtain a pure or semi-pure fermentation product enriched in insecticidally active dunaimycins.

Another aspect of this invention is a method for screening actinomycetes for insecticidal activity by measuring the amount of active and inactive dunaimycins produced by a library of dunaimycin over-producing actinomycetes. In one embodiment of this method, the screening step is preceded by a step in which a library of mutant dunaimycin-over-producing actinomycetes is created from a parent dunaimycin-producing strain.

BRIEF DESCRIPTION OF THE DRAWINGS

FIG. 4 provides the results for the bioactivity of a Rifampcin-resistant mutant vs wild-type stage 3 screening assay, with LD50 data.

DETAILED DESCRIPTION OF THE INVENTION

Figure 1:
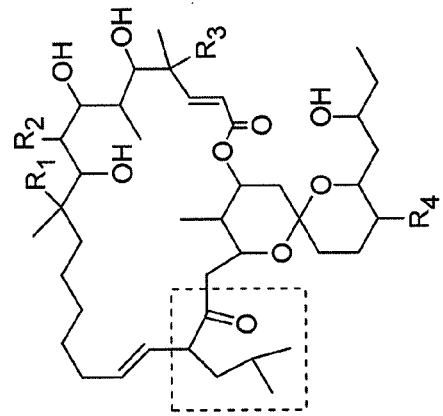
FIG. 1 provides a general structure for the dunaimycins described herein, including those identified as A1, C1, C2, C2S, D2, D2S, D3, D3S and D4S. See descriptions of activities of various dunacimycins on pages 5-6 and in Table 1 of Example 2 on page 14.

This invention relates to insecticidal actinomycete-produced fermentation broths and related fermentation solids that contain an optimized ratio of insecticidally active to inactive dunaimycins. The term "fermentation broth" refers to the culture medium resulting after fermentation of a microorganism and encompasses the microorganism and its component parts, unused raw substrates, and metabolites produced by the microorganism during fermentation, among other things. The term "fermentation solid," as used herein, refers to concentrated and/or dried fermentation broth. The term "crude extract," as used herein, refers to organic extracts of fermentation broth, such as ethyl acetate extracts. The term "semi-purified," as used herein, refers to metabolites isolated from fermentation broth that are about 50% to about 90% pure. The term "purified," as used herein, refers to metabolites that are isolated from fermentation broth that are about 91% to about 100% pure.

The actinomycete in the fermentation broth produces both insecticidally active and inactive dunaimycins and may be a strain of *Streptomyces*. Several previously identified strains of *Streptomyces* produce multiple species of dunaimycins. Such strains include *Streptomyces* galbus NRRL No. 30232, described in U.S. Pat. No. 6,682,925 and *Streptomyces diastatochromogenes* strains AB1691Q-321 and AB1711J-452, described in Karwowski, J. P., et al, *Journal of Antibiotics* December 1991, p. 1312. In addition, strains of *Streptomyces* can be readily screened for ability to produce active and inactive dunaimycins using techniques described herein and known in the art.

Dunaimycin-producing actinomycetes may also be mutants of dunaimycin-producing parent strains, such as isolated wild type strains. Mutants may be obtained by physical and chemical methods known in the art. For example, mutant strains may be obtained by treatment with chemicals such as N-methyl-N-nitro-N-nitrosoguanidine. Spontaneous mutants may be obtained without the intentional use of mutagens by, for example, classical methods, such as growing the parent strain in the presence of a certain antibiotic to which the parent is susceptible and testing any resistant mutants for improved biological activity or, in this application, overproduction of dunaimycins compared to the parent. Mutants may also be obtained by producing protoplast fusions of strains that produce dunaimycins, using the techniques described in Keiser, T., et al. *Practical Streptomyces Genetics*, 2000, pp. 57-58. Mutants that produce more dunaimycins than the parent strain are referred to herein as "dunaimycin-overproducing strains." In some embodiments, such dunaimycin-overproducing strains produce about 2 to about 20 times more dunaimycins than the parent strain.

In one embodiment, such a mutant is *Streptomyces galbus* M1064. This mutant was obtained by screening for antibiotic-resistant, dunaimycin-overproducing mutants of *Streptomyces galbus* NRRL No. 30232, as described in detail in Example 1. M1064 was deposited on Nov. 5, 2009 in the USDA's Agricultural Research Service Patent Culture Collection located at 1815 N. University Street Peoria, Ill. 61604 U.S.A. (NRRL) in accordance with the Budapest Treaty on the International Recognition of the Deposit of Microorganisms for the Purpose of Patent Procedure and the Regulations thereunder (Budapest Treaty) and was assigned Accession No. NRRL 50334. This strain has been deposited under conditions that assure that access to the cultures will be available during the pendency of this application. However, it should be understood that the availability of a deposit does not constitute a license to practice the subject invention in derogation of patent rights granted by governmental action.

The general structure of dunaimycins and various species of dunaimycins are shown in FIG. 1. The term "active dunaimycin" as used herein refers to those dunaimycin species that are insecticidally active. In one embodiment, purified active dunaimycin species are insecticidally active against at least some insects at a concentration of less than about 1000 ppm; in another at a concentration of less than about 500 ppm; in yet another at a concentration of less than about 200 ppm. Active dunaimycins include D3S, C2S, D2, D2S, D4S and C2. The term "inactive dunaimycin" as used herein refers to those dunaimycin species that are insecticidally inactive. Purified inactive dunaimycin species do not show insecticidal activity against some or all insects and are inactive up to about 1000 ppm. Inactive dunaimycins include A1 and C1. In one embodiment, insecticidal activity is determined by activity against Lepidopterans. In another embodiment, active and inactive dunaimycins are distinguished by the ability of each to show insecticidal activity against beet army worm with an LD50 of 200 ppm or less.

Figure 2:
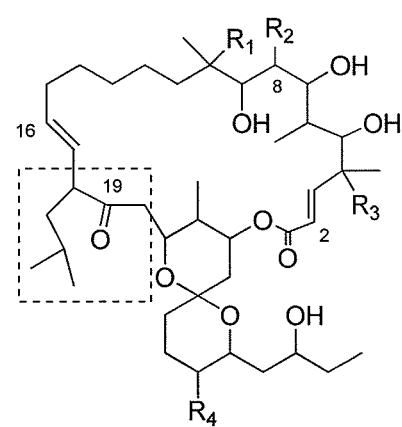
FIG. 2 provides a numbering scheme for the dunaimycins described herein.

In some embodiments, active dunaimycins have a vinylogous enol ether or hemiacetal or acetal moiety at position C18-C19, as do D2S, C2S, D2, D2S and C2. Numbering of carbons in the dunaimycins is shown in FIG. 2. In such embodiments, inactive dunaimycins lack these moieties and instead have a ketone at position C19, as do A1 and C1. Without intending to be bound by any specific theory, Applicants believe that the presence of the vinylogous enol ether or the hemiacetal or acetal moiety is needed for biological activity, while presence or absence of the amino sugar moiety at the $R_2$ position shown in FIG. 2 is not essential to activity but increases the molecule's water solubility. One further consideration is that the active dunaimycins bind agonistically (that is, as activators) to specific protein targets in the insect while inactive dunaimycins competitively inhibit binding of the active species, but themselves exhibit only weak effects on these protein targets.

In one embodiment, the fermentation broth includes at least about 0.5 g total dunaimycin per liter. In another embodiment, it includes at least about 1 gram total dunaimycin per liter. In yet another embodiment, it includes at least 3 grams total dunaimycin per liter of broth. In still another embodiment, it includes at least 7 grams total dunaimycin per liter of broth. In another embodiment, the fermentation broth includes between about 1 gram and about 7 grams total dunaimycin per liter of broth.

In one embodiment, the optimized ratio of active to inactive dunaimycins is at least about 1:1. In another embodiment, the optimized ratio of active to inactive dunaimycins is at least about 2:1. The ratio can be calculated based on either a molar or weight ratio of the dunaimycins. For example, dunaimycins A1 and C1 do not have a sugar component, while dunaimycins D2S and D3S have an attached sugar. The sugar-containing dunaimycins are about 10% by weight heavier than those without sugar and do not appreciably impact the overall ratios of active to inactive dunaimycins.

Compositions of the present invention include the above-described fermentation broth, which may be used as is, or dried and/or concentrated. The fermentation broth or fermentation solids may be formulated with one or more carriers. If necessary for the end use, the fermentation broth may be treated to inactivate the microorganism by heat, chemical, or irradiation means before formulation. Carriers are inert formulation ingredients added to the fermentation broth to improve recovery, efficacy, or physical properties and/or to aid in packaging and administration. Such carriers may be added individually or in combination. In some embodiments, the carriers are anti-caking agents, anti-oxidation agents, bulking agents, and/or protectants. Examples of useful carriers include polysaccharides (starches, maltodextrins, methylcelluloses, proteins, such as whey protein, peptides, gums), sugars (lactose, trehalose, sucrose), lipids (lecithin, vegetable oils, mineral oils), salts (sodium chloride, calcium carbonate, sodium citrate), and silicates (clays, amorphous silica, fumed/precipitated silicas, silicate salts). In some embodiments, the carriers are added after concentrating fermentation broth and during and/or after drying.

In one embodiment, the compositions include fermentation solids that are formulated as wettable powders or water dispersible granules in which the fermentation solid is present at a concentration of about 1% to about 90% by weight.

In another embodiment, the compositions may be formulated as emulsifiable concentrates in which concentrated fermentation broth is dissolved in an inert carrier which is either a water-miscible solvent or mixture of a water-immiscible organic solvent and emulsifiers. The concentrated fermentation broth is present at a concentration of about 10% to about 90%.

In another embodiment, the compositions may be formulated as an aqueous suspension, in which the concentrated fermentation broth or the fermentation solid is dispersed in an aqueous vehicle at a concentration in the range of from about 0.1% to about 50% by weight.

Certain methods are useful for preparing fermentation broths having an optimized ratio of active to inactive dunaimycins. In one aspect of this invention, the above-described fermentation broth is produced by culturing a dunaimycin-producing actinomycete in a suitable culture medium optimized to enhance production of active dunaimycins and to minimize production of inactive dunaimycins. Suitable culture media may be obtained by adjusting the ratio of nitrogen source to carbon source, such that there is more nitrogen available than carbon in the culture media. In one embodiment, the ratio of carbon to nitrogen is between about 1:1 to about 200:1. In another, the ratio is between about 10:1 to about 30:1. In another, the ratio is about 20:1. As noted in the Summary above, the indicated ratios are for the relative weight amounts of C and N in the sources. In one embodiment, a batch process is carried out in which the ratio is set during the batching (before starting fermentation) and is not adjusted during fermentation. In another embodiment, consumption of C and N sources is monitored and additions are made to the fermentation medium during the process.

Selection of specific carbon and nitrogen sources may also be used to optimize the ratio of active to inactive dunaimycins. Suitable carbon sources include monosaccharide, disaccharides, and polysaccharides, such as glucose, fructose, sucrose, molasses, maltodextrin, and starch, and plant-derived fatty acids and oils such as soy oil and cotton seed oil. Suitable nitrogen sources may be microbial, animal and plant derived proteins and amino acids or substances containing proteins. In one embodiment, the nitrogen source comes from soy-derived products, such as soy flour, soytone, soy hydrolysate, and soy grits. In another embodiment the nitrogen source includes cotton-seed derived products, such as PROFLO (Traders Protein, Lubbock, Tex.) and martone (Marcor Development Corporation, Carlstadt, N.J.), corn steep powder, malt extract, and potato extract. In yet another embodiment, the nitrogen sources are animal-derived, such as casein derived products (skim milk, casein peptone, casein hydrolysate, casamino acids) and peptone. In yet another embodiment, the nitrogen sources are microbial-derived, such as yeast extracts or whole yeasts. Other essential elements necessary for growth and development of the organism should also be included in the culture medium and will be well known to those of skill in the art.

Monitoring the levels of C and N in the fermentation medium can be carried out using conventional methods to monitor the carbon and/or nitrogen sources. For example, glucose levels can be monitored using a Beckman Glucose Analyzer, sucrose can be monitored using an enzymatic (invertase) method, while more complex sources (for example, molasses and malt extracts) can be analyzed by a colorimetric reducing sugar method after acid hydrolysis of a fermentation media aliquot.

Conventional large-scale microbial culture processes including submerged fermentation, solid state fermentation, or liquid surface culture may be used to cultivate dunaimycin-producing actinomycetes. Dunaimycins are produced when grown at temperatures between about 20° C. and about 32° C. In one embodiment, pH of the fermentation broth is maintained between about 6 and about 8.

In one embodiment, the dunaimycin-producing actinomycete is cultivated until at least about 1 gram dunaimycins per liter fermentation broth are produced or, in another embodiment, until at least about 2 grams dunaimycins per liter are produced, or in still another embodiment until at least about 3 grams dunaimycins per liter fermentation broth are produced, or in yet another embodiment until about 1 gram to about 7 grams dunaimycins per liter are produced. Production of dunaimycins can be following during the fermentation by testing extracts of the broth. One method for following production is analysis of extracts by high performance liquid chromatography (HPLC).

In one embodiment, the above method for producing an insecticidal fermentation broth having an optimized ratio of active to inactive dunaimycins includes a further step of concentrating the broth by conventional industrial methods, such as centrifugation, membrane filtration, tangential-flow filtration, depth filtration, and evaporation. In some embodiments, the concentrated fermentation broth is washed, for example via a membrane dialysis or ultra-filtration process, to remove residual fermentation broth.

In another embodiment, the fermentation broth or broth concentrate can be dried with or without the addition of carriers using conventional drying processes or methods such as spray drying, freeze drying, tray drying, fluidized-bed drying, or drum drying. The resulting fermentation solids may be further processed, such as by milling or granulation, to achieve a specific particle size or physical format.

In another aspect of the invention, the insecticidal fermentation broth produced by the above process is chemically treated in order to modify the inactive dunaimycins, so that they are unable to interfere or compete with active dunaimycins for biologically relevant binding sites or targets or so that they are transformed into active dunaimycins. In one embodiment, selected dunaimycins can be removed from the mixture. For example, removal of dunaimycins A 1 and C1 can be accomplished by passing the entire mixture of all dunaimycins thru a resin with a pendant amino functional group such as a primary amine, oxime, semicarbazide, or hydrazine. The C19-keto group present in A1 and C1 will react preferentially with the pendant amino group and the remaining dunaimycins can be removed from the column by simply washing with an appropriate solvent. Dunaimycins containing, for example, the ossamine sugar moiety can be removed by passing the dunaimycin mixture thru a cation exchange resin. The amino group present on the ossamine sugar will help retain the active dunaimycin molecules having the sugar on the column, and allow for the inactive dunaimycins to pass thru. The active ossamine sugar dunaimycins can then be eluted out of the resin with basic buffer.

In another embodiment, inactive dunaimycins can be reduced in the mixture by genetic manipulation of the actinomyces strains to specifically knock out the expression of the inactive dunaimycin either by classical genetics or by molecular means.

In yet another aspect of the invention, the insecticidal fermentation broth produced by the above process is subjected to standard purification techniques in order to separate active dunaimycins from inactive dunaimycins and obtain semi-purified or purified dunaimycins.

The present invention also encompasses methods for screening actinomycetes for the ability to preferentially produce active dunaimycins. In one embodiment the ratio of active dunaimycins to inactive dunaimycins produced by actinomycetes of interest is greater than about 1:1. In another embodiment, no inactive dunaimycins are produced. In another aspect of the invention, the screening step is preceded by generation of a library of dunaimycin-overproducing strains. For example, Examples 1 and 2 describe producing a library of mutants and using chromatography methods to identify those that over-produce dunaimycins. Other methods for rapid screening of mutants that are over-producers of dunaimycin include creating a colorimetric reporter strain.

The compositions of this invention are useful for control of insects. Therefore, a further aspect of the present invention is directed to methods for controlling an insect by applying to the locus of the insect an effective amount of the compositions of the present invention. As used herein, the term "control" or "controlling" means to kill insects or to decrease the number of viable insect eggs. The term "locus" means the environment in which the insect lives or where its eggs are present, such as plant parts or the area surrounding plants which the insect might eat or inhabit. An "effective amount" is the amount needed to cause a measurable reduction of the treated insect. In some embodiments, greater than about 50% control is obtained, in others greater than about 60%; in others greater than about 70%; in others greater than about 75%; in others, greater than about 80%.

In one embodiment, rates of about 100 ppm to about 10000 ppm of fermentation solids per acre are used. In another embodiment, between about 1 and about 50 g of formulated fermentation solids are applied per acre.

In one embodiment, the compositions are used to control Lepidoptera, such as tobacco budworm (*Heliothis virescens*), beet armyworm (*Spodoptera exigua*), cabbage looper (*Trichoplusia ni*) and diamondback moth (*Plutella xylostella*). Other typical Lepidoptera are Egyptian cotton leaf worm, oblique banded leafroller, black cutworm, pandemis leafroller, codling moth, fall armyworm, and corn earworm.

EXAMPLES

Example 1

Production of Mutant

QST6047 (*Steptomyces galbus* NRRL No. 30232) is a wild strain of *Streptomyces galbus* that produces a suite of dunai-mycins. The dunaimycins produced by QST6047 have insecticidal activity against Lepidoptera. With the goal to increase dunaimycin production and bioactivity, a dunaimycin over-producing mutant M1064 was created from the wild strain QST6047 through an antibiotic-resistant mutant screening program in which libraries of mutants resistant to individual antibiotics (gentamicin, rifampicin, streptomycin, paromomycin or tobramycin) were produced. A detailed description of creation and screening of the rifampicin-resistant library, from which a dunaimycin-overproducing strain was ultimately selected for further development, is described below.

Spores from a SFM (Mannitol 20 g/L, soy flour 20 g/L, agar 20 g/L) plate culture of *S. galbus* QST6047 suspended in 20% glycerol were heat shocked for ten minutes in a 50° C. water batch. 100 µl of the spore suspension was then plated onto GYM (glucose 4 g/L, yeast extract 4 g/L, malt extract 10 g/L, and agar 12 g/L) supplemented with 5 µl/ml rifampicin. Enough spore suspension was plated in order to have at least 300 individual colonies to isolate, purify, and screen.

Figure 3:
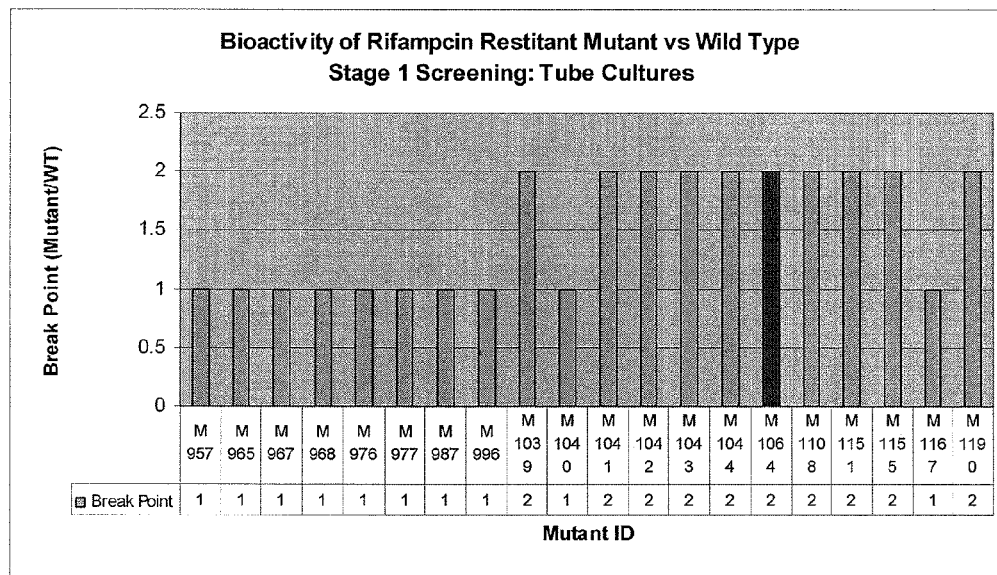
FIG. 3 provides the results for the bioactivity of a Rifampcin-resistant mutant vs wild-type stage 1 screening assay.

Agar plugs containing rifampicin-resistant bacteria were used to inoculate culture tubes that contained 31-3C medium (Proflo 20 g/L, malt extract 20 g/L, $KH_2PO_4$ monobasic 6 g/L, $K_2HPO_4$ dibasic 4.8 g/L) and grown for six days at 28 C. The culture broth was then serially diluted and tested for bioactivity using a beet army worm egging bioassay (BAW Egging Bioassay) as follows. The test samples were distributed across a 96-well microplate containing beet army worm (BAW) eggs. The each well of the microplates contained diet and about known number of beet army worm eggs. The microplate was incubated under optimal conditions for the eggs to hatch. After seven days, the number of worms still living were counted and a break point rating was assigned. The break point of the mutant relative to the break point of the wild type was noted. Each break point represented a 2× increase in activity over wild type. Any mutant exhibiting bioactivity above the wild type was then cultured in shake flasks. Of 300 mutants screened, 20 showed increased bioactivity (FIG. 3).

Figure 5:
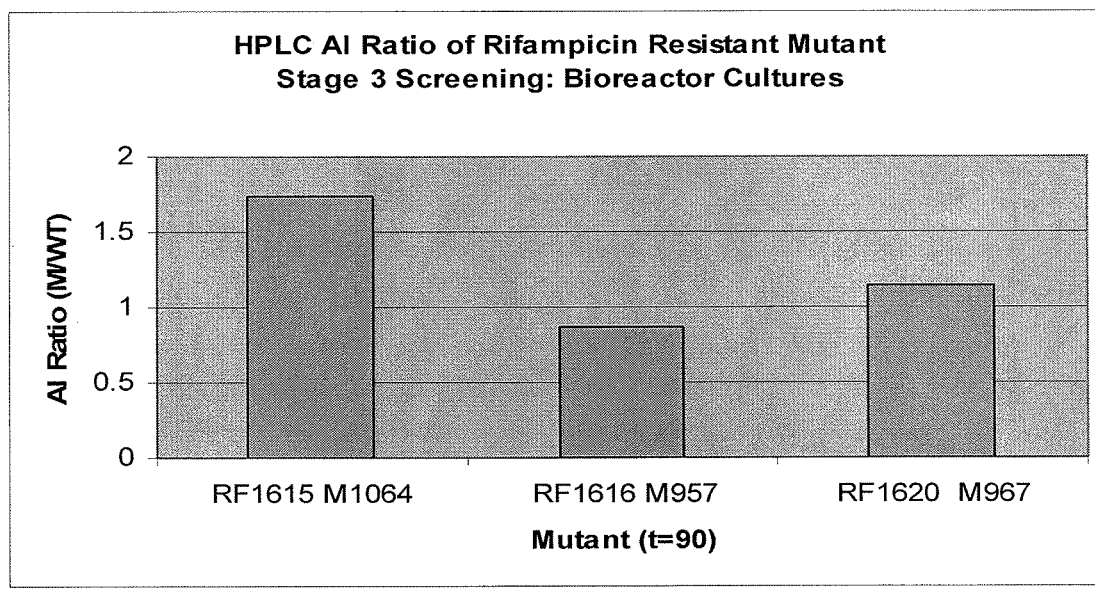
FIG. 5 provides the results of a HPLC determination of AI ratios of Rifampicin-resistant mutant stage 3 screening.

Selected mutants with higher bioactivity and ability to sporulate on agar plates were grown in 1-L baffled shake flasks and subsequently scaled up to 20-L bioreactors containing 31-3C media. Both bioactivity (FIG. 4) and dunaimycin production (FIG. 5) were measured for each mutant. Surprisingly, although the mutants produced higher levels of dunaimycins than the wild type, the bioactivity did not increase proportionally.

Example 2

Identification of the Potency Differences in Bioactivities of Various Dunaimycins (HPLC Identification and Bioassays)

The various species of dunaimycins were isolated from either a mutant called M1064 or wild type (Streptomyces galbus QST6047) for analysis of activity. Either M1064 or wild type was grown up in 2 L flasks using the media described above. The whole broth culture was extracted twice with 1 L ethyl acetate and the combined organic extract concentrated under reduced pressure. The crude extract was loaded onto a silica gel column equilibrated in hexanes, and the column was eluted with hexanes followed by a step solvent gradient of hexanes-ethyl acetate. The fractions containing the dunaimycins were determined by analytical HPLC reverse-phase C8 column and BAW egging bioassay.

Figure 6:
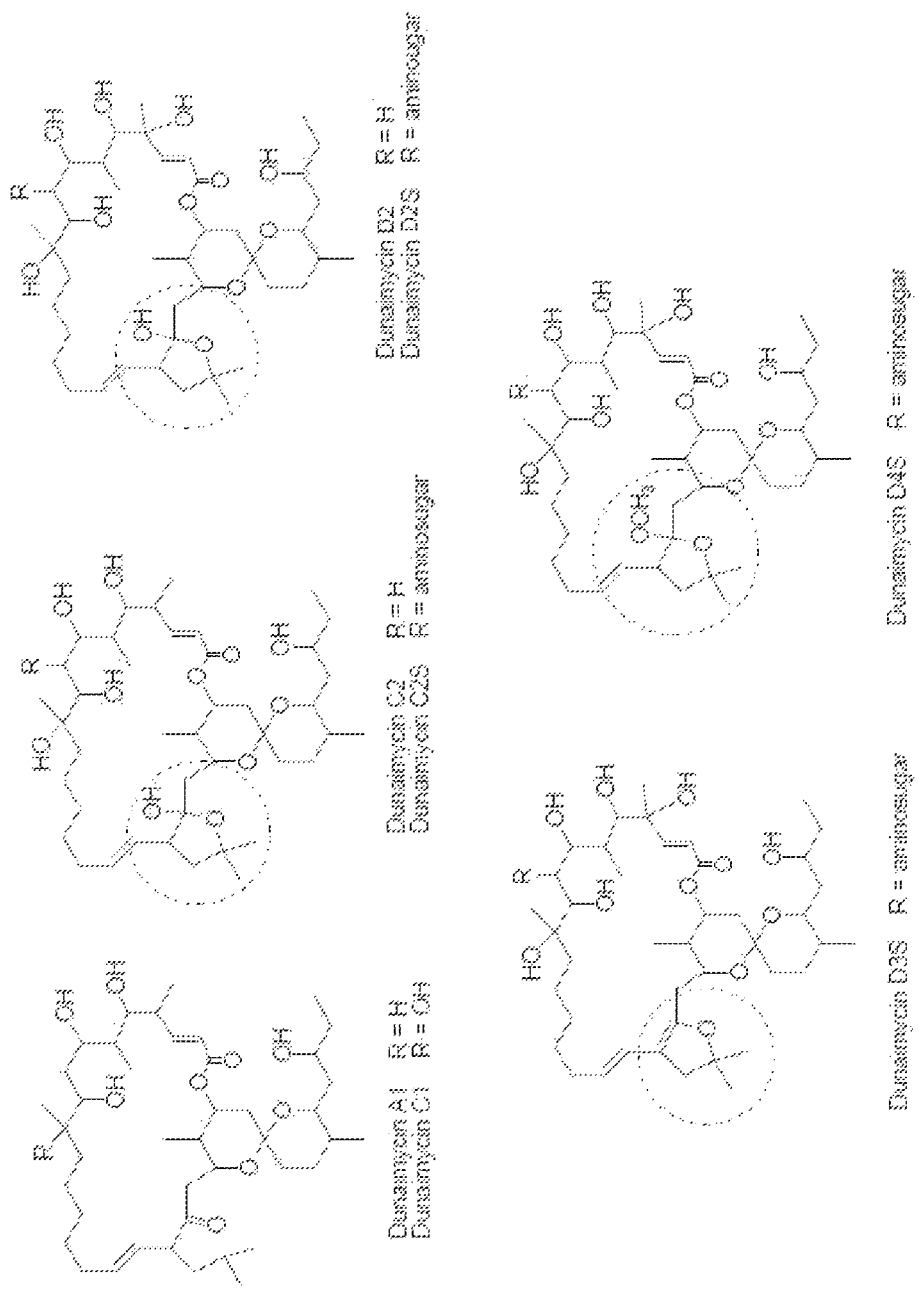
FIG. 6 provides specific structures of dunaimycins referred to herein as A1, C1, C2, C2S, D2, D2S, D3S and D4S. The structure of the dunaimycin referred to herein as D3 is not provided in FIG. 6 but can be determined from FIG. 1.
Figure 7:
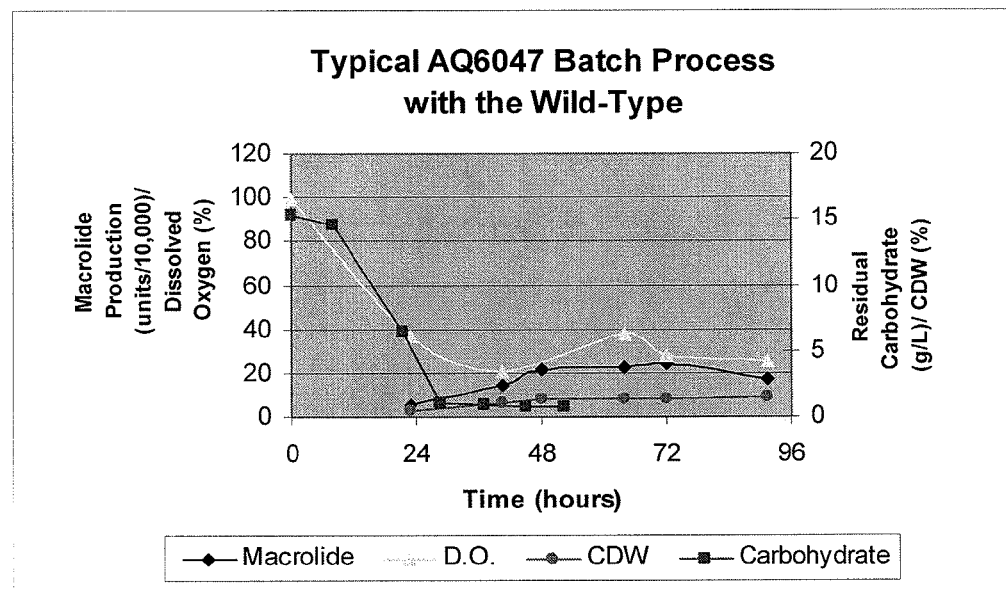
FIG. 7 provides a graph showing macrolide production for a typical batch process for AQ6047 with wild-type.
Figure 8:
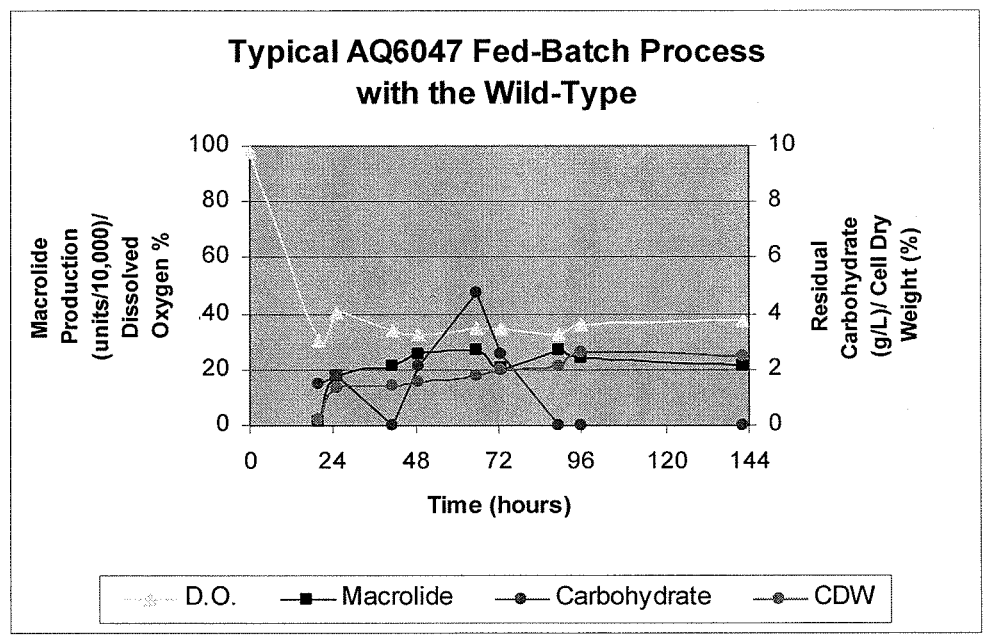
FIG. 8 provides a graph showing macrolide production for a typical fed-batch process for AQ6047 with wild-type.
Figure 9:
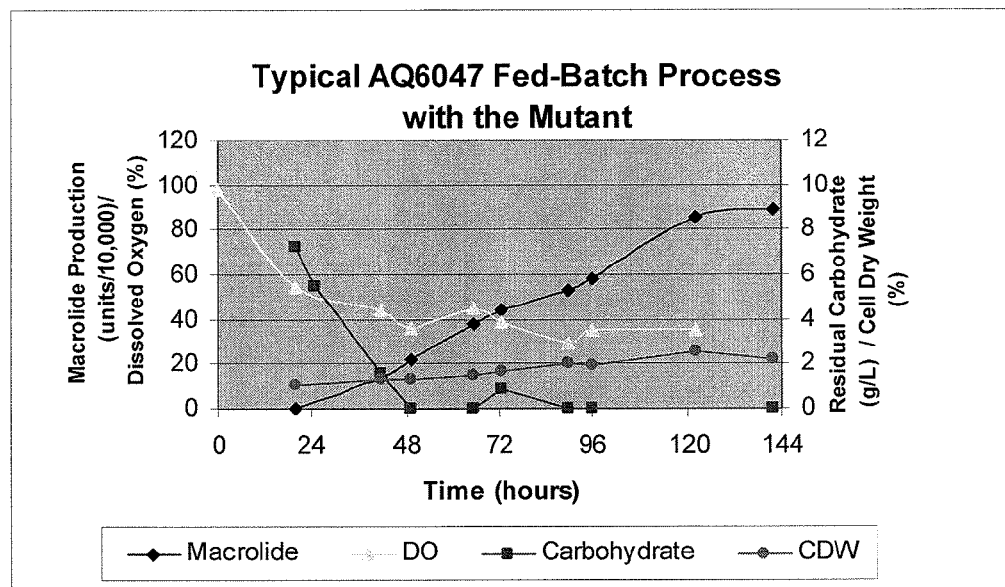
FIG. 9 provides a graph showing macrolide production for a typical fed-batch process for AQ6047 with mutant.
Figure 10:
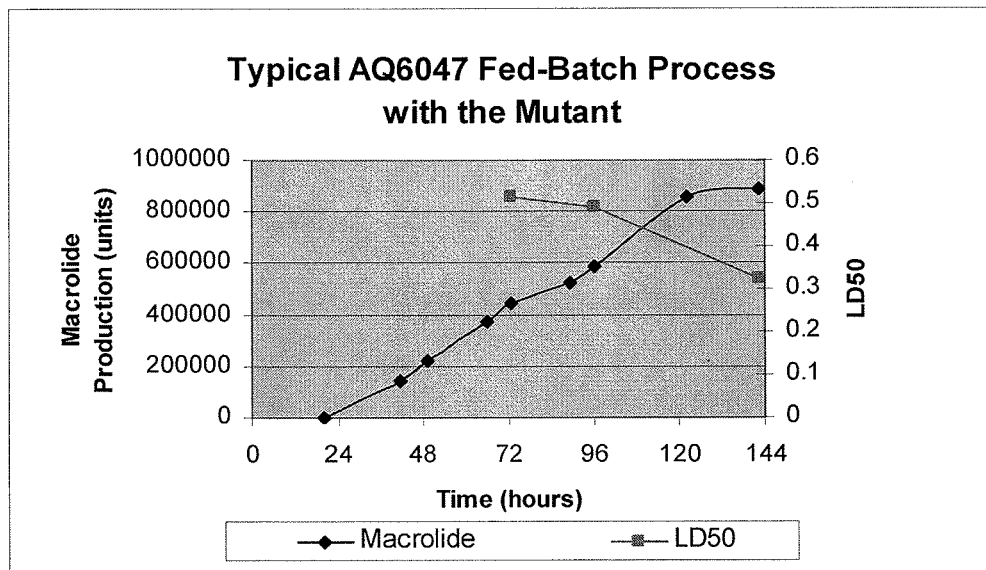
FIG. 10 provides a graph showing dunaimycins production and corresponding bioactivities of M1064 in fed-batch fermentation.
Figure 11:
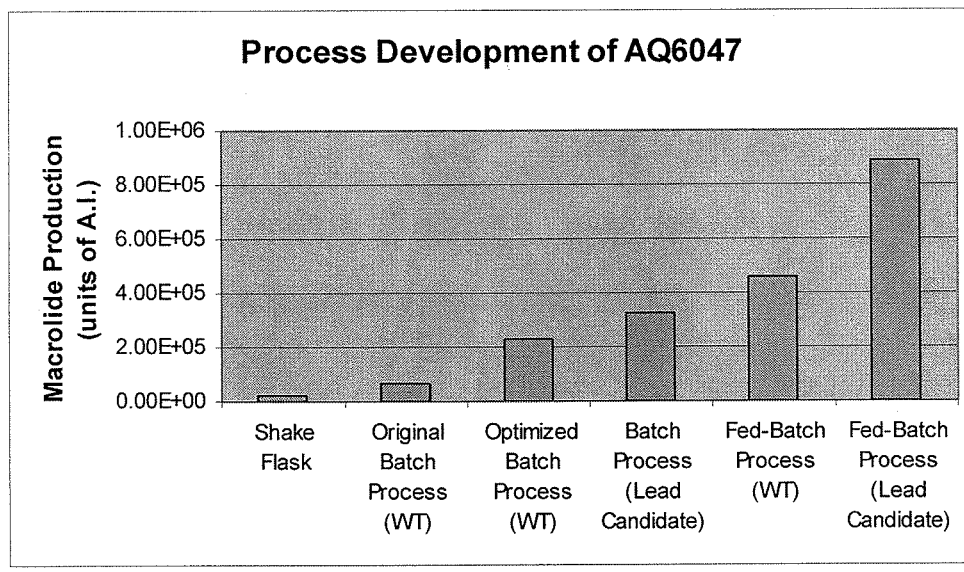
FIG. 11 provides a graph showing improvement in dunaimycins production through fermentation optimization.

Active fractions were further fractionated using a preparative reverse-phase C8 column [Zorbax Exclipse XDB-C8, 5

μm; 9.4×25 cm at a flow rate of 2.0 mL/min and UV detection at 220 nm. Eluting solvent system consisted of water (10 mM $NH_4OAc$):methanol mixture] which yielded pure dunaimycins. All isolated dunaimycins were confirmed using UV and mass spectrometry. Structures of identified dunaimycins are shown in FIG. 6.

The separated, identified dunaimycins were then tested for bioactivity against beet armyworm eggs as follows. Stock solutions were provided as 15% aqueous ethanol solution of various semipurified dunaimycins, either alone or in combinations. For reference purposes, Javelin WDG (*Bacillus thuringiensis* subspecies *Kurstaki*; ThermoTrilogy Inc) was weighed out and diluted to give a 1,000 ppm stock solution (positive chemical standard). These stock solutions were transferred to a deep well microtitre plate: 1.4 ml of each stock solutions were placed in the 2 ml well across the top row (A wells 1-12). A Packard Multiprobe II liquid handling system (Perkin Elmer Inc.) then carried out a dilution program, first adding 700 μls of DI $H_2O$ to the remaining 84 wells (B-H 1-12). The four tip arm then performed a sequence of aspiration and dispensing steps to mix the samples and then transferred them into an adjoining well to give eight 50% serially diluted samples containing 700 μl per well. The robot then used a transfer program to pipette all of the serial diluted samples to labeled 96 well plates. Aliquots containing 40 μl of each dilution were dispensed into six wells across a microtitre plate containing ~200 μl of artificial diet/well. Two samples were tested on every 96 well plate; Sample one at the stock concentration in wells A1-6; sample two into wells A7-12. Row B contains a 50% dilution series or a ½ X solution of sample one in row B wells 1-6 and sample two in row B wells 7-12. The last two samples in each set were the chemical standard and untreated controls containing DI water. The samples were dried rapidly at room temperature under forced air and then each well was egged with 5-10 synchronized beet army worm eggs in agar using a repeating pipette. The egg: agar mixture is dried under forced air and the plates were covered with perforated Mylar. The plates were incubated at 28° C. on a 16:8 light:dark cycle. After five to seven days the number of live insects in each row was tabulated. Mortality was recorded as the number dead over the number treated and expressed as control corrected percent mortality. The data was exported from Excel into Polo PC (LeOra Software 1987) and LC 10, 50, and 90s were calculated using natural response and 95% confidence intervals. Results are shown in Table 1.

TABLE 1

Bioactivity of purified dunaimycins and combinations

| Compound | Ratio | LD50 (ppm) BAW assay |
|---|---|---|
| Dunaimycin A1 | Tested alone | Inactive up to 1000 ppm |
| Dunaimycin C1 | Tested alone | Inactive up to 1000 ppm |
| Dunaimycin C2 | Tested alone | 31 |
| Dunaimycin C2S | Tested alone | 10 |
| Dunaimycin D2/D2S | Tested alone | 11 |
| Dunaimycin D3S | Tested alone | 9 |
| A1:D2/D2S | 1:1 | 107.8 |
| A1:D2/D2S | 4:1 | 150.1 |
| A1:D2/D2S | 8:1 | 239.6 |
| D2/D2S:C2:C1:A1 | 2.6:1:3.75:5.1 | 156.1 |
| A1:C1 | 1:1 | Inactive up to 1000 ppm |
| D2/D2S:C2 | 2.57:1 | 25.1 |

Example 3

Fermentation Optimization (Including Fermentation and Related Bioassays)

Initial fermentation optimization studies focused on improving the fermentation process for QST6047 and for the mutant M1064 to increase total dunaimycin production, as described below. (Further studies with M1064, also described below, focused on optimizing production of active dunaimycins.) Improvements associated with strain improvement and fermentation optimization studies were tracked simultaneously by bioassays for insecticidal activity and by HPLC for dunaimycin production. The bioassay employed a Multi-PROBE® II automated liquid handling system, and a 96-well-plate assay using beet armyworm on an artificial diet followed by Probit analysis of the raw data. The bioactivity is reported as the lethal concentration of sample needed to kill 50% of the worm population (LC50). The HPLC assay utilized a partition extraction of the whole broth followed by C-18 reverse phase chromatography and peak integration analysis (mAU).

Under optimal temperature, pH, aeration and agitation, a three fold increase in the QST6047 strain's dunaimycin production was achieved over the original batch fermentation process. A profile of typical growth parameters and dunaimycin production for QST6047 in an optimized batch process is presented in FIG. 7. (In the Figures the term macrolide is equivalent to dunaimycin and the term lead candidate is equivalent to M1064.) To further improve macrolide production, a fed-batch process was developed. Several different feeding strategies were investigated. A process was developed in which carbohydrate was batched during sterilization and a variable feed rate with additional carbohydrate and nitrogen was initiated later on in the process to maintain residual carbohydrate levels at concentrations less than 1 g/L. This fed-batch process resulted in a two fold increase in the QST6047 strain's dunaimycin production over the optimized batch process. A profile of typical growth parameters and macrolide production for the wild-type optimized fed-batch process is presented in FIG. 8.

Fermentation conditions were also optimized for increased dunaimycin production of M1064. Media rebalancing and refining of batch process parameters was necessary to determine the optimum conditions for macrolide production, and a 1.5 fold increase in macrolide production over the wild-type batch process was achieved. The most significant increase in macrolide production was achieved with M1064 by employing a fed-batch process. Similar to the wild-type fed-batch process, some carbohydrate was initially present at the start of the process. Variable feed rates with additional carbohydrate and nitrogen was initiated later on in the process to maintain residual carbohydrate levels at concentrations less than 1 g/L. Slower feed rates than with the wild-type were used due to a slower carbohydrate consumption rate by the mutant. With a fed-batch process, a 13 fold increase in dunaimycin production was achieved over the original wild-type batch process. A profile of typical dunaimycin production, growth parameters, and carbohydrate utilization for a fed-batch process with M1064 is presented in FIG. 9. A profile of dunaimycin production and the corresponding bioactivity for M1064 is presented in FIG. 10. FIG. 11 shows the increase in dunaimycin production during the optimization process.

Additional media development and process studies were conducted to increase bioactivity of M1064 by optimizing the ratios of active dunaimycins and inactive dunaimycins. Various carbon and nitrogen sources were used to culture the mutant M1064 and the wild type. It was found that different carbon and nitrogen sources can have different effects on the production of active and inactive dunaimycins and that relative ratio between active and inactive can have significant impact on the insecticidal activity. Glucose and soy flour were the carbon and nitrogen sources particularly useful for improving the ratios between active to inactive dunaimycins. See Tables 2 and 3 below.

TABLE 2

| Carbon | % Active Dunaimycins | % Inactive Dunaimycins | Ratio Active/Inactive | LC50 |
|---|---|---|---|---|
| Sucrose | 31 | 41 | 0.76 | 0.26 |
| Glucose | 43 | 20 | 2.15 | 0.15 |
| Molasses | 31 | 43 | 0.72 | 0.90 |
| Malt Extract | 33 | 51 | 0.64 | 0.65 |

TABLE 3

| Condition | Culture | % Active Dunaimycins | % Inactive Dunaimycins | Ratio Active/ Inactive | LC50 |
|---|---|---|---|---|---|
| Batch w/o soy flour | WT | 41 | 28 | 1.46 | 0.31 |
| Batch w/soy flour | WT | 48 | 24 | 2.0 | 0.26 |
| Batch w/o soy flour | M1064 | 33 | 50 | 0.66 | 0.65 |
| Batch w/soy flour | M1064 | 36 | 11 | 3.27 | 0.24 |

After identifying optimal sources for carbon and nitrogen, further bioreactor studies were focused on the optimization of the fermentation process, particularly on the batch and fed-batch processes. It was discovered that, in addition to the sources of carbon and nitrogen, the C:N ratio of the fermentation media also had significant impact on the level of active dunaimycin production and the bioactivity.

TABLE 4

C:N ratios of the batch and fed-batch fermentation processes

| Fermentation process | Nitrogen (g) | Carbon (g) | C:N ratio |
|---|---|---|---|
| Batch | 2.7 | 53.1 | 20:1 |
| Fed-batch | 1.9 | 24.3 | 13:1 |

The following are descriptions of the optimized batch and fed-batch processes for M1064 using the above C:N ratios.

Batch Fermentation Process Seed Train

The first stage seed was prepared by thawing a frozen vial of the culture and dispensing half of its contents into two, 250 ml baffled flasks containing 50 ml of sterile 31-3C seed media (Table 5). The culture was incubated at 28° C. on a shaker at 220 rpm for three days.

The second stage seed was prepared by transferring 10 ml of the three day old first stage seed to a 2-liter baffled flask containing 250 ml of 31-3C seed media. The cultures were incubated at 28° C. on a shaker at 220 rpm for three days. Three 2-liter flasks were prepared for each fermentation which had a working volume of 15 liters.

Fermentation Media and Conditions

The media ingredients for the 15 L fermentation process were weighed and suspended in the bioreactor in 14-liters of distilled water. The media ingredients for the M1064 process 352 are presented in Table 6. The media was thoroughly mixed and the pH adjusted to 7.3. After sterilization, the media was re-adjusted to pH 6.8.

Fermentation Process—20-Liter Bioreactor

The contents from three 2-liter flasks (750 ml) of three-day-old second-stage-seed was pooled and used to inoculate a sterile bioreactor. The cultures were streaked onto nutrient agar to confirm culture purity. The pH was controlled at 6.8 throughout the fermentation. The cultivation temperature was 25° C. and the rate of aeration was 15 L/min. The dissolved oxygen concentration was controlled at 50% with an agitation cascade between 300 and 850 rpm. The fermentation was conducted for 90-95 hours with samples taken twice a day to monitor the process.

Analytical Methods for Growth, Dunaimycin and Bioactivity

Growth was monitored by % solids, % cell dry weight and occasionally colony forming units. Glucose concentration was monitored using the Beckman glucose analyzer.

The total dunaimycins present per ml of whole broth was quantified by HPLC. Sample extracts were prepared by combining 5 ml of whole broth with 3 ml of ethyl acetate and 2 g of magnesium sulfate.

Bioactivity of the whole broth was measured by using the BAW egging bioassay described in Example 1. Javelin was run as the positive control at an initial concentration of 1000 ppm. The LD50 was then calculated.

TABLE 5

Seed Media (31-3C)

| Ingredient | g/L |
|---|---|
| Proflo cottonseed meal | 20.0 |
| Malt Extract | 20.0 |
| $KH_2PO_4$ | 6.0 |
| $K_2HPO_4$ | 4.8 |

TABLE 6

Fermentation Media for Process M1064

| Ingredient | g/L |
|---|---|
| Proflo cottonseed meal | 20.0 |
| Glucose | 50.0 |
| Soyflour | 10 |
| Soy Oil | 5.0 |
| Sigma 204 Antifoam | 1.0 |

Fed-Batch Fermentation Process

Seed Train

The first stage seed was prepared by thawing a frozen vial of the culture and dispensing half of its contents into two, 250 ml baffled flasks containing 50 ml of sterile 31-3C seed media (Table 7). The culture was incubated at 28° C. on a shaker at 220 rpm for three days.

The second stage seed was prepared by transferring 10 ml of the three day old first stage seed to a 2-liter baffled flask containing 250 ml of 31-3C seed media. Three 2-liter flasks were inoculated for each fermentation run which had a working volume of 15 liters. The cultures were incubated at 28° C. on a shaker at 220 rpm for three days.

Fermentation Media and Conditions The media ingredients for the 15 L fermentation process were weighed and suspended in the bioreactor in 14-liters of distilled water. The media ingredients for the 6047 wild type process 328 are presented in Table 8. The media was thoroughly mixed and the pH adjusted to 7.3. After sterilization, the media pH was re-adjusted to 6.8.

Fermentation Process—20-Liter Applikon Bioreactor

The contents from three 2-liter flasks (750 ml) of three-day-old second-stage-seed were pooled and used to inoculate the sterile bioreactor. The cultures were streaked onto nutrient agar to confirm culture purity. The pH was controlled at 6.8 throughout the fermentation. The cultivation temperature was 25° C. and the rate of aeration was 15 L/min The dissolved oxygen concentration was controlled at 50% with an agitation cascade between 300 and 850 rpm. The fermentation was conducted for 90-95 hours with samples taken twice a day to monitor the process using the analytical methods described below.

Feeding Regime

A feed of 30% glucose was initiated at the start of cultivation. The goal was to aggressively feed glucose such that little to no glucose was detected in the bioreactor. After 24 hours, a feed of 30% glucose and 3% monosodium glutamate was implemented. Feed rates were based on glucose consumption and increased or decreased based on the residual glucose concentration of the media.

Analytical Methods for Growth, Dunaimycin Production and Bioactivity

Growth was monitored by % solids, % cell dry weight. Cell dry weight of the washed pellet was monitored by using a Saterius moisture balance. Glucose concentration was monitored using the Beckman glucose analyzer.

The total dunaimycins present per ml of whole broth was quantified by HPLC. Sample extracts were prepared by combining 5 ml of whole broth with 3 ml of ethyl acetate and 2 g of magnesium sulfate.

Bioactivity of the whole broth was measured against beet army worm using the BAW egging bioassay described in Example 1 in the Batch fermentation process section of this example.

TABLE 7

| Seed Media (31-3C) | |
| --- | --- |
| Ingredient | g/L |
| Proflo cottonseed meal | 20.0 |
| Malt Extract | 20.0 |
| $KH_2PO_4$ | 6.0 |
| $K_2HPO_4$ | 4.8 |

TABLE 8

| Fermentation Media for M1064 | |
| --- | --- |
| Ingredient | g/L |
| Proflo cottonseed meal | 20.0 |
| Malt Extract | 20.0 |
| Soy Oil | 5.0 |
| Sigma 204 Antifoam | 1.0 |
| Glucose Feed Stock | |
| Dextrose | 300.0 |
| Monosodium Glutamate Feed Stock | |
| Ingredient | g/200 ml |
| Monosodium glutamate | 60 |

Bioassay results obtained following fermentation optimization (including studies regarding C:N ratio) confirmed that bioactivity of M1064 was substantially increased compared to the wildtype 6047. The strain improvement and optimized fed batch process described above gave rise to a 13 fold increase in dunaimycin production compared to the original fermentation process used with 6047 and to a 35 fold increase in bioactivity, based on BAW egging assay, as compared to whole broth from the original fermentation process with 6047.

Example 4

Bioactivity Comparison of M1064 Grown with and without Soy Flour

Figure 12:
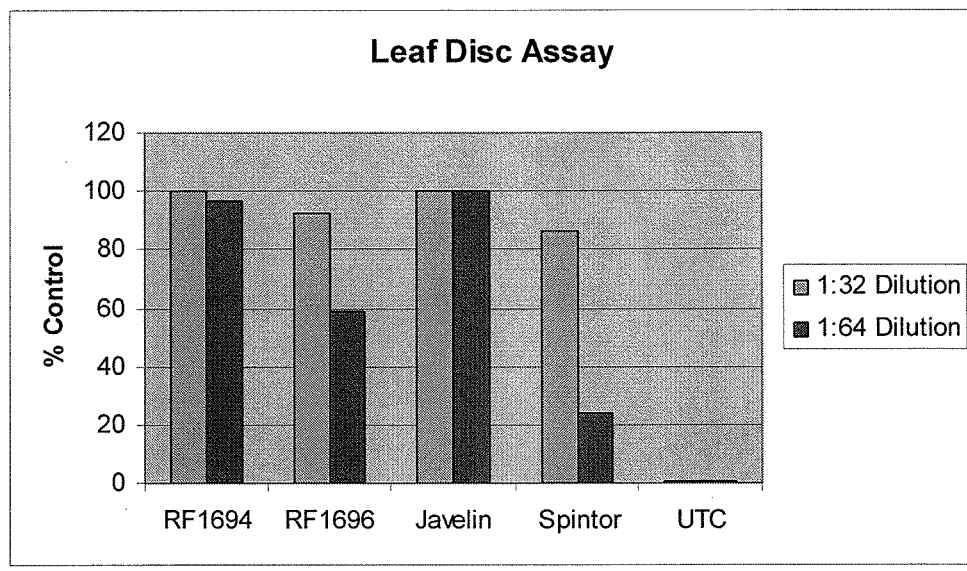
FIG. 12 provides a graph showing bioactivities against beet army worm by fermentation broth of RF 1694 and RF 1696 along with Javelin (a *Bacillus thuringensis* product) Spintor (a spinosyn-based product) and untreated control (UTC).

Batch fermentation RF1694 with the addition of soy flour and RF1696 without the soy flour were conducted on M1064 under the same conditions described at the end of Example 3. Whole broth from both fermentation runs were analyzed for dunaimycin production (Table 9) by HPLC and for insecticidal activities on beet army worm using a leaf disc assay (FIG. 12). The leaf disc assay was performed on lima bean leaves. The whole broth from RF1694 with soy flour had higher bioactivity than RF1694 at both the 1:32 and the 1:64 dilutions in the bioassay. The assay was performed with untreated control (UTC) and along with commercial insecticide Javelin (a Bt based product) and Spintor (Dow Agro-Sciences; a spinosyn-based product).

Although the total dunaimycin produced was similar between the two runs, the amounts of active and inactive dunaimycins were different. Less of the inactive forms of dunaimycin was produced in the batch RF1694 which contained soy flour, which resulted in higher ratio of active to inactive.

TABLE 9

Active and inactive dunaimycins produced in bioreactors.

| | | Total | Active | Inactive | Ratio Active:Inactive |
| --- | --- | --- | --- | --- | --- |
| RF1694 | With Soy flour | 648009 | 224672 | 169832 | 1.32 |
| RF1696 | Without Soy flour | 549549 | 210613 | 210857 | 0.99 |

What is claimed is:

1. A composition comprising an insecticidal fermentation broth or solid from an actinomycete wherein the fermentation broth or solid comprises an optimized ratio of active dunaimycins to inactive dunaimycins whereby the optimized ratio provides insecticidal activity at less than 1000 ppm.

2. The composition of claim 1, wherein the optimized ratio of active dunaimycins to inactive dunaimycins is at least about 1:1.

3. The composition of claim 1, wherein the concentration of active dunaimycins and inactive dunaimycins is at least about 1 g/L of fermentation broth.

4. The composition of claim 1, wherein the concentration of active dunaimycins and inactive dunaimycins is at least about 3 g/L of fermentation broth.

5. The composition of claim 1, wherein the concentration of active dunaimycins and inactive dunaimycins is at least about 7 g/L of fermentation broth.

6. The composition of claim 1, wherein the actinomycete is a *Streptomyces* sp, strain that produces both active dunaimycins and inactive dunaimycins.

7. The composition of claim 6, wherein the *Streptomyces* sp, strain is *Streptomyces galbus*.

8. The composition of claim 6, wherein the *Streptomyces* sp, strain is *Streptomyces* sp. M1064.

9. The composition of claim 1, further comprising a carrier.

10. The composition of claim 1, wherein the active dunaimycins have a vinylogous enol ether or hemiacetal or acetal moiety at position C18-C19 and the inactive dunaimycins have a ketone at position C19.

11. The composition of claim 10, wherein the active dunaimycin is one or more of C2, C2S, D2, D2S and D3S and the inactive dunaimycin is one or more of A1 and C1.

* * * * *